US008389661B2

(12) United States Patent
Soula et al.

(10) Patent No.: US 8,389,661 B2
(45) Date of Patent: *Mar. 5, 2013

(54) COMPLEXES BETWEEN AN AMPHIPHILIC POLYMER AND AN OSTEOGENIC PROTEIN BELONGING TO THE FAMILY OF BMPS

(75) Inventors: Gerard Soula, Meyzieu (FR); Olivier Soula, Meyzieu (FR); Remi Soula, Lyon (FR)

(73) Assignee: ADOCIA, Lyons (FR)

( * ) Notice: Subject to any disclaimer, the term of this patent is extended or adjusted under 35 U.S.C. 154(b) by 0 days.

This patent is subject to a terminal disclaimer.

(21) Appl. No.: 12/219,679

(22) Filed: Jul. 25, 2008

(65) Prior Publication Data

US 2009/0048412 A1    Feb. 19, 2009

Related U.S. Application Data

(60) Provisional application No. 60/952,407, filed on Jul. 27, 2007.

(30) Foreign Application Priority Data

Jul. 27, 2007  (FR) ...................... 07 05536

(51) Int. Cl.
*A61K 31/765* (2006.01)
*A61K 31/74* (2006.01)
*C08F 251/00* (2006.01)

(52) U.S. Cl. .............. 527/200; 527/312; 424/78.37; 424/78.27; 424/423; 424/78.17; 424/489

(58) Field of Classification Search .......... 527/300–315, 527/200; 424/486, 489, 499, 502, 401, 433, 424/436, 450, 78.24, 78.37, 78.17, 94.63; 514/12, 54, 102, 59
See application file for complete search history.

(56) References Cited

U.S. PATENT DOCUMENTS

| | | | |
|---|---|---|---|
| 2,808,405 A | 10/1957 | Novak et al. | |
| 5,750,678 A | 5/1998 | Bauer et al. | |
| 5,977,076 A | 11/1999 | Anderson et al. | |
| 6,258,382 B1 | 7/2001 | Takaoka et al. | |
| 6,573,251 B2 | 6/2003 | Barritault et al. | |
| 6,617,456 B1 | 9/2003 | Tsujihara et al. | |
| 6,646,120 B1 | 11/2003 | Chaubet et al. | |
| 2001/0000470 A1* | 4/2001 | Bernstein et al. | 424/433 |
| 2004/0131583 A1* | 7/2004 | Barritault et al. | 424/78.27 |
| 2004/0132653 A1 | 7/2004 | Ichikawa et al. | |
| 2004/0208844 A1* | 10/2004 | Ignatious | 424/78.17 |
| 2005/0209145 A1 | 9/2005 | Stupp et al. | |
| 2005/0287135 A1* | 12/2005 | Li et al. | 424/94.63 |
| 2006/0233841 A1 | 10/2006 | Brodbeck et al. | |
| 2008/0102128 A1* | 5/2008 | Constancis et al. | 424/489 |
| 2008/0234227 A1 | 9/2008 | Soula et al. | |

FOREIGN PATENT DOCUMENTS

| | | |
|---|---|---|
| DE | 41 36 324 A1 | 5/1993 |
| EP | 1 454 640 A2 | 9/2004 |

OTHER PUBLICATIONS

Abbatiello et al.; "Anion-Mediated Precipitation of Recombinant Human Bone Morphogenetic Protein (rhBMP-2) is Dependent Upon the Heparin Binding N-Terminal Region;" *Protein Science; The Protein Society: Eleventh Symposium*; Boston MA; Jul. 12-16, 1997.
Schlunegger et al.; "Refined Crystal Structure of Human Transforming Growth Factor β2 at 1.95 Å Resolution;" *Journal of Molecular Biology*; 1993; pp. 445-458; 231.
Yeung et al.; "Direct Isoform Analysis of High-Mannose-Containing Glycoproteins by On-Line Capillary Electrophoresis Electrospray Mass Spectrometry;" *Analytical Chemistry*; 1997; pp. 2510-2516; 69, 13.
Urist; "Bone: Formation by Autoinduction;" *Science*; 1965; pp. 893-899; 150.
Israel et al; "Heterodynamic Bone Morphogenetic Proteins Show Enhanced Activity In Vitro and In Viva;" *Growth Factors*; 1996; pp. 291-300; 13.
Ruppert et al.; "Human bone morphogenetic protein 2 contains a heparin-binding site which modifies its biological activity;" *European Journal of Biochemistry*; 1996; pp. 295-302; 237.
Sanchez-Chaves; "Poly (vinyl alcohol) funtionalized by monosuccinate groups. Coupling of bioactive amino compounds;" *Polymer*. 1998; pp. 2751-5757; 39, 13.
Scheufler et al.; "Crystal Structure of Human Bone Morphogenetic Protein-2 at 2.7 Å Resolution;" *Journal of Molecular Biology*; 1999; pp. 103-115; 287.
Shah et al.; "High-resolution Morphometric Analysis of Human Osteoblastic Cell Adhesion on Clinically Relevant Orthopedic Alloys;" *Bone*; 1999; pp. 499-506; 24, 5.
Saito et al.; "A biodegradable polymer as a cytokine delivery system for inducing bone formation;" *Nature Biotechnology*; 2001 pp. 332-335; 19.
Cheng et al.; "Osteogenic Activity of the Fourteen Types of Human Bone Morphogenetic Proteins (BMPs);" *The Journal of Bone and Joint Surgery*; 2003; pp. 1544-1552; 85A, 8.
Schmoekel et al.; "Bone healing in the rat and dog with nonglycosylated BMP-2 demonstrating low solubility in fibrin Matrices;" *Journal of Orthopaedic Research* 2004; pp. 376-381; 22.
Chen et al.; "Bone Morphogenetic Proteins;" *Growth Factors*; 2004; pp. 233-241; 22, 4.

(Continued)

*Primary Examiner* — James J Seidleck
*Assistant Examiner* — S. Camilla Pourbohloul
(74) *Attorney, Agent, or Firm* — Oliff & Berridge, PLC

(57) ABSTRACT

The invention relates to an amphiphilic-BMP polymer complex which is physically and chemically stable and soluble in water, characterized in that:
the amphiphilic polymers comprise a hydrophilic polysaccharide skeleton functionalized with hydrophobic substituents and hydrophilic groups
the BMP is selected from the group of therapeutically active BMPs (Bone morphogenetic Proteins),
the polymer/BMP mass ratio is lower than or equal to 700.
The invention also relates to the process for preparing the amphiphilic-BMP polymer complex in an aqueous medium and in the absence of organic solvents likely to denature the protein.
The invention also relates to therapeutic compositions of an amphiphilic-BMP polymer complex according to the invention.

26 Claims, No Drawings

OTHER PUBLICATIONS

Schmoekel et al.; "Bone Repair with a Form of BMP-2 Engineered for Incorporation Into Fibrin Cell Ingrowth Matrices;" *Biotechnology and Bioengineering*; Dec. 2004; pp. 253-262; 89,3.

Schwartz et al; "Development of an Aqueous Suspension of Recombinant Human Bone Morphogenetic Protein-2 (rhBMP-2);" 2005; pp. 1-126.

Durand et al., "Aqueous Solutions of Native and Hydrophobically Modified Polysaccharides: Temperature Effect," Biomacromolecules, vol. 7, 2006, pp. 958-964.

Durand et al., "Neutral amphiphilic polysaccharides: chemical structure and emulsifying properties," *Colloid Polym. Sci.*, vol. 284, 2006, pp. 536-545.

Heinze et al., "Functional Polymers Based on Dextran," *Adv. Polym. Sci.*, vol. 205, 2005, pp. 199-291.

Stryer, L., (1988) "Biochemistry," published by W. H. Freeman and Company, New York, pp. 16-20.

Machine translation of DE 41 36 324 A1 (published on May 13, 1993), retrieved from <http://ep.espacenet.com> on Jan. 3, 2011.

Office Action mailed Jan. 20, 2011 in U.S. Appl. No. 12/078,441.

* cited by examiner

COMPLEXES BETWEEN AN AMPHIPHILIC POLYMER AND AN OSTEOGENIC PROTEIN BELONGING TO THE FAMILY OF BMPS

The present invention relates to the formation of water-soluble original complexes between an amphiphilic polymer and an osteogenic protein belonging to the family of bone morphogenetic proteins (BMPs), which complexes are physically and chemically stable and therefore improve the physical and chemical stability of BMPs, both in vitro and in vivo.

Bone morphogenetic proteins (BMPs) are growth factors involved in mechanisms of osteoinduction. BMPs, also known as osteogenic proteins (OPs), were initially characterised by Urist in 1965 (Urist MR. Science 1965; 150, 893). These proteins, which are isolated from cortical bone, are able to induce the formation of bone in a wide variety of animals (Urist MR. Science 1965; 150, 893).

The BMPs are expressed in the form of propeptides which, after post-translational maturation, have a length between 104 and 139 residues. Their sequences are very homologous and they have similar three-dimensional structures. In particular, they have six cysteine residues involved in intramolecular disulphide bonds forming a "cysteine knot" (Scheufler C. 2004 J. Mol. Biol. 1999; 287, 103; Schlunegger MP, Mol. Biol. 1993; 231, 445). Some of them have a seventh cysteine which is also involved in an intermolecular disulphide bond which leads to the formation of a dimmer (Scheufler C. 2004 J. Mol. Biol. 1999; 287:103.).

In their active form, the BMPs are assembled as homodimmers and even as heterodimmers, as has been described by Israel et al. (Israel DI, Growth Factors, 1996, 13(3-4), 291). Dimeric BMPs interact with BMPR-type transmembrane receptors (Mundy et al. Growth Factors, 2004, 22 (4), 233). This recognition sets off a cascade of intracellular signalisation involving, in particular, Smad proteins, thus resulting in the activation or repression of target genes. With the exception of BMPs 1 and 3, BMPs play a direct and indirect role in differentiating mesenchymatous cells, resulting in differentiation thereof into osteoblasts (Cheng H., J. Bone and Joint Surgery, 2003, 85A 1544-1552). They also have properties of chemotaxis and induce proliferation, differentiation and angiogenesis.

Some human recombinant BMPs and, in particular, rhBMP-2 and rhBMP-7 have clearly shown an ability to induce bone formation in vivo in humans and have been approved for some medical applications. Thus, human recombinant BMP-2, or dibotermin alfa according to the international non-proprietary name, is formulated in products sold under the name InFuse® in the United States and under the name InductOs® in Europe. This product is prescribed for the fusion of lumbar vertebrae and for bone regeneration of the tibia for what are known as non-union fractures. In the case of InFuse® for the fusion of lumbar vertebrae, the surgical procedure involves, first of all, drenching a collagen sponge in a rhBMP-2 solution, then placing the sponge in a hollow cage (LT Cage) previously implanted between the vertebrae.

Human recombinant BMP-7, or eptotermin alfa according to the international non-proprietary name, has the same therapeutic indications as BMP-2 and forms the base of two products, namely the OP-1 Implant for open fractures of the tibia and OP-1 Putty for the fusion of lumbar vertebrae. OP-1 Implant consists of a powder containing rhBMP-7 and collagen to be taken up in a 0.9% saline solution. The paste obtained is then applied to the fracture during a surgical procedure. OP-1 Putty is present in the form of two powders, one containing rhBMP-7 and collagen, the other containing carboxymethyl cellulose (CMC). During the surgical procedure, the CMC is reconstituted with a 0.9% saline solution and mixed with the rhBMP-7 and the collagen. The paste thus obtained is applied to the site to be treated.

Among all the proteins currently sold, BMPs stand out due to their high hydrophobicity and their ability to aggregate which leads to very low solubility at physiological pH. In the case of BMP-2, these properties have been documented within the scope of studies for the purposes of clinically developing BMP-2. It is not very soluble in physiological conditions and tends to aggregate (Schmoekel, 2004 J. Orthop. Res. 2004; 22(2), 376, Friess, W., Drug Delivery Systems Based on Collagen, Shaker Verlag, Thesis Aachen Germany 1999, Schwartz D H, Thesis Muïchen Germany 2005). Thus Abbatiello and Porter (Protein Sci. 1997, 6, Suppl 2 99) have shown that, in a buffer of low ionic strength, BMP-2 becomes more and more insoluble when the pH is higher than 4.5. Precipitation of the protein is observed at a pH greater than 6.5 but also at a lower pH in the presence of chloride and/or sulphate ions (pH 5.8 with 50 mM NaCl and ph 5.5 with 5 mM $Na_2SO_4$) as has been shown by Friess (Friess, W., Drug Delivery Systems Based on Collagen, Shaker Verlag, Thesis Aachen Germany 1999). The formulation of BMP-2 in physiological conditions is therefore a problem in its own right.

Another example of this problem of physical instability of BMPs is revealed by Biopharm in patent US2004132653 with a protein from the sub-class of BMP-14, GDF-5 for Growth and Differentiation Factor, also known as MP-52. The properties of GDF-5 are very similar to those of BMP-2 and instability of lyophilisate, which tends to condense and not be able to be entirely redissolved during reconstitution of the solution, has been observed. These two phenomena are linked to an irreversible aggregation of proteins. In order to solve this problem, mannitol is added before lyophilisation and thus makes it possible to prevent these problems in solid state. However, mannitol only provides a low level of stability in vitro and does not prevent physical instability in vivo.

Taking into account the constraints imposed by the physical properties of these growth factors, the product InFuse® has had to be formulated at an acidic pH (acetic acid buffer, pH 4) and in the presence of a surfactant (Polysorbate 80) in order to ensure the solubility and physical stability of rhBMP-2.

Manufacturers of therapeutic protein-based drugs are very much affected by the problems of physical stability of proteins. In fact, the formation of BMP aggregates may lead to:
  a reduction in the number of biologically active species,
  changes in the bioactivity or rate of absorption,
  a potential immunological response to said aggregates,
  an undesirable appearance due to opalescence of the product,
  an obstruction of filtration equipment and injection devices.

In order to obtain the desired therapeutic effect, it is necessary to use very substantial therapeutic doses of BMP which are greater by a factor of 10,000 than the physiological dose.

This is particularly the case when it comes to the treatment of vertebral fusion with a product such as InFUSE® since several milligrams of rhBMP-2 are administered. This large amount of BMP to be administered means having to work at increased concentrations of BMP in solution, approximately 1.5 mg/ml. At these concentrations, the BMPs aggregate rather easily and are therefore physically unstable. The solutions supplied use acid buffers and surfactants. However, with regard to therapeutic application, the use of a solution which is acidic and contains surfactants is problematic.

Several approaches have been developed in order to solve these problems of physical and chemical stability.

Firstly, heparin and heparan sulphates are well-known for stabilising growth factors, including BMs, since these polysaccharides are endogenous stabilisation molecules (Ruppet et al. Eur. J. Biochem. 1996, 237, 295). However, heparin and heparan sulphates have a very considerable anti-coagulant and anti-complementary activity and therefore cannot be used in a pharmaceutical composition.

Hubbell described a method for grafting the protein which involves creating a chemical bond between the protein and a vector so as to stabilise said protein in a fibrin-type matrix. Said bond is established by means of a fusion protein which can be cleaved by enzymes. This method, reported in publication Biotechno. Bioeng. 2005, 89, 3, 253, makes it possible, in fact, to physically stabilise the protein by preventing aggregation. However, said method leads to use of an analogue of BM-2, of which the therapeutic efficacy and safety have yet to be demonstrated.

In patent US20050209145, Stupp et al. describe amphiphilic peptides for the vectorisation of growth factors and, in particular, the vectorisation of BM-2. Said amphiphilic peptides are formed of a terminal alkyl chain, a hydrophilic peptide sequence and an epitope enabling adhesion of BM-2. Said peptides are arranged in solution so as to form rod-type macromolecular structures, at the heart of which hydrophobic groups are aggregated. The amino acids at the periphery allow compatibility with water and adhesion of the protein. However, said peptides present an immunological risk due to their complex primary structure.

In patent U.S. at. No. 6,258,382, Takaoka et al. dealt with the vectorisation of BM for bone regeneration applications. The authors developed new lactic acid and/or glycolic acid-based, p-dioxanone-based and glycolic polyethylene-based polymers enabling the release of said proteins to be controlled. However, the authors do not address any of the problems linked to said growth factor in terms of physical or chemical stability. Moreover, said polymers are not soluble in water but adsorb the water and form gels. On the other hand, said polymers are soluble in an organic medium and are solubilised in acetone. The preparation of the polymer-BM-2 formulation thus requires the use of an organic solvent, which risks denaturing the protein (Nature Biotechnology, 2001, 19, 332).

In patent US2005/0287135, Wyeth describes hyaluronans modified by a hydrophobic group (benzylic alcohol) for the vectorisation of BMs. In these polymers, the content of hydrophobic groups is between 50 and 100% so the polymer is not soluble in water but may adsorb water. In this case, said hygroscopic polymers cannot form a water-soluble complex with the protein, thus solving the problems of stability of BMs. Formulations of this type are also disclosed in E 1454640 in the name of the Fidia et Genetics Institute; the formulations disclosed, however, do not form complexes, and the polysaccharides exemplified are insoluble in water and comprise more than 50% of a hydrophobic ester group.

In patent NZ530701, Brodbeck et al. use LAGAs for the vectorisation of BMs. Said polymers are insoluble in water and therefore cannot form a water-soluble complex with the protein. The object of the authors is, in contrast to the applicant, to insolubilise, in an aqueous medium, the BM in a solid formed of LAGA, which still requires use of an organic solvent which risks denaturing the protein.

By way of example, the studies by Blanquaert et al. and Barritault et al., published under the title "Effects of heparin-like polymers associated with growth factors on osteoblast proliferation and phenotype expression", 1998, J. Biomed. Mater. Res., vol 44, p. 63-72, describe the use of dextrans modified by benzylamine which are believed to interact with various growth factors. The polymers are described as having a therapeutic activity. The authors also claim that some of these dextrans and, more particularly, the dextrans substituted with carboxymethyl (CM), benzylamide (B) and sulphonate (S) groups, (CMDBS compounds) enable stimulation of bone reconstruction without the addition of a growth factor (1999, Bone, 17, 6, 499-506).

According to a similar method, in patent FR2794649, Blachant et al. describe dextrans modified by benzylamine and sulphates insolubilised by cross-linking polymer chains using trimethyl phosphate. These sponges in an aqueous medium act as BM reservoirs since they are able to hold on to this protein. Before cross-linking, the amphiphilic polymers form complexes with the BM-2, as shown in a test of interaction by way of gel electrophoresis. However, the polymer/BM mass ratios used are very high—greater than 5,000. These high ratios are used due to a rather weak polymer/protein interaction which leads to dissociation of the complex in solution. Also, the chemical or physical stabilisation of BM is not documented. Ratios of this type are unacceptable for the development of a pharmaceutical product.

It is also known that benzylamine may have a particular toxicity and may be detrimental to the biocompatibility of the polymers described in the two patents mentioned above.

The galenic formulation of proteins of this type for bone reconstruction must inevitably satisfy the safety requirements of excipients and, in order to satisfy these requirements, it is necessary to use compounds which are biocompatible but also to limit the quantity thereof in relation to the active ingredient.

Thus, the problem of developing injectable formulations enabling solubilisation and stabilisation of osteogenic proteins, such as BMs selected from the group consisting of BM-2 (dibotermin-alfa), BM-4, BM-7 (eptotermin-alfa), BM-14 and GDF-5, is not resolved in a satisfactory manner.

The present invention enables the formation of a stable water-soluble complex between osteogenic proteins and an amphiphilic polymer which is biocompatible at a polymer/BM mass ratio lower than 700. This complex makes it possible to:
avoid aggregation of BMs, which occurs due to their hydrophobicity at physiological pH in vitro and in vivo,
stabilise BMs in the presence of cells at 37° C.

Said water-soluble complex is formed in a completely aqueous medium without the need to use an organic solvent.

The present invention thus relates to an amphiphilic-BM polymer complex which is physically and chemically stable and soluble in water, characterised in that:

the amphiphilic polymers are formed of a hydrophilic polysaccharide skeleton functionalised with hydrophobic substituents and hydrophilic groups according to the following general formula I:

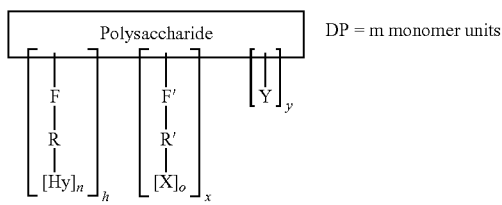

R, R', which may be the same or different, represent a bond or a chain comprising between 1 and 18 carbon atoms, said chain optionally being branched and/or unsaturated and comprising one or more heteroatoms, such as O, N or/and S, F, F', which may be the same or different, represent an ester, a thioester, an amide, a carbonate, a carbamate, an ether, a thioether or an amine, X represents a hydrophilic group selected from the group consisting of carboxylates, sulphates, sulphonates, phosphates and phosphonates, Y represents a hydrophilic group selected from the group consisting of sulphates, sulphonates, phosphates and phosphonates, Hy represents a hydrophobic group selected from the group consisting of:

linear or branched $C_8$ to $C_{30}$ alkyls which may be unsaturated and/or contain one or more heteroatoms, such as O, N or S.

linear or branched $C_8$ to $C_{18}$ alkylaryls or a linear or branched $C_8$ to $C_{18}$ arylalkyl which may be unsaturated and/or may contain one or more heteroatoms such as O, N or S.

$C_8$ to $C_{30}$ polycycles which may be unsaturated and/or may contain one or more heteroatoms, such as O, N or S, excluding benzylamine.

n and o are between 1 and 3, h represents the mole fraction of a hydrophobic pattern with respect to a monomer unit, between 0.01 and 0.5 x represents the mole fraction of hydrophilic groups with respect to a monomer unit, between 0 and 2.0 y represents the mole fraction of hydrophilic groups with respect to a monomer unit, between 0 and 0.5 the BMP is selected from the group of therapeutically active BMPs (bone morphogenetic proteins), the polymer/BMP mass ratio is lower than or equal to 700.

In one embodiment, in the complex according to the invention the polysaccharide is selected from the polysaccharides of general formula I, as defined above, in which y=0.

In one embodiment, in the complex according to the invention the polysaccharide is selected from the polysaccharides of general formula I, as defined above, in which X is a carboxylate.

In one embodiment, in the complex according to the invention the polysaccharide according to the invention is characterised in that the group R is selected from the following groups:

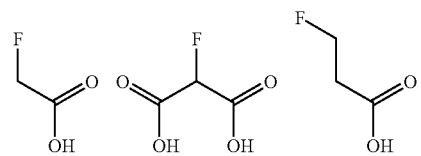

In one embodiment, the invention relates to a complex characterised in that the polymer/BMP mass ratio is lower than or equal to 600.

In one embodiment, the invention relates to a complex characterised in that the polymer/BMP mass ratio is lower than or equal to 500.

The concentration of BMP for therapeutic use is approximately 1.5 mg/ml in solution. When the ratio is greater than 700, compositions comprising 1.0 g/ml of amphiphilic polymer are obtained. Based on said polymer concentrations, the formulations have a physicochemical behaviour which is no longer suitable for a pharmaceutical application, for example with regard to viscosity.

The invention relates to a complex characterised in that the BMP is selected from the group consisting of BMP-2 (dibotermin-alfa), BMP-4, BMP-7 (eptotermin-alfa), BMP-14 and GDF-5.

The substituents of the amphiphilic polymers are distributed in a controlled or statistical manner. Block copolymers and alternating copolymers are examples of polymers which have a controlled distribution of substituents.

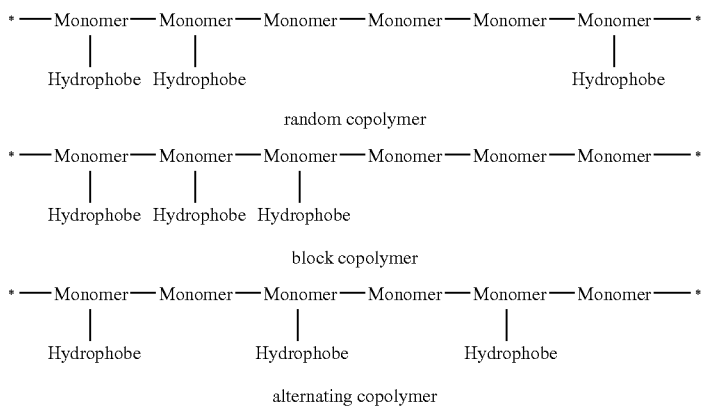

Thus, in one embodiment, the invention also relates to an amphiphilic-BMP polymer complex characterised in that the polymer is selected from polymers of which the substituents are distributed in an arbitrary manner.

In one embodiment, the polysaccharides are selected from the group consisting of the hyaluronans, the alginates, the chitosans, the galacturonans, chondroitin sulphate, the dextrans and the celluloses.

The group of celluloses consists of celluloses functionalised with acids, such as carboxymethyl cellulose.

The group of dextrans consists of dextrans functionalised with acids, such as carboxymethyl dextran.

In one embodiment, the polysaccharides are selected from the group consisting of the hyaluronans, the alginates and the chitosans.

These various polysaccharides may be represented as follows:

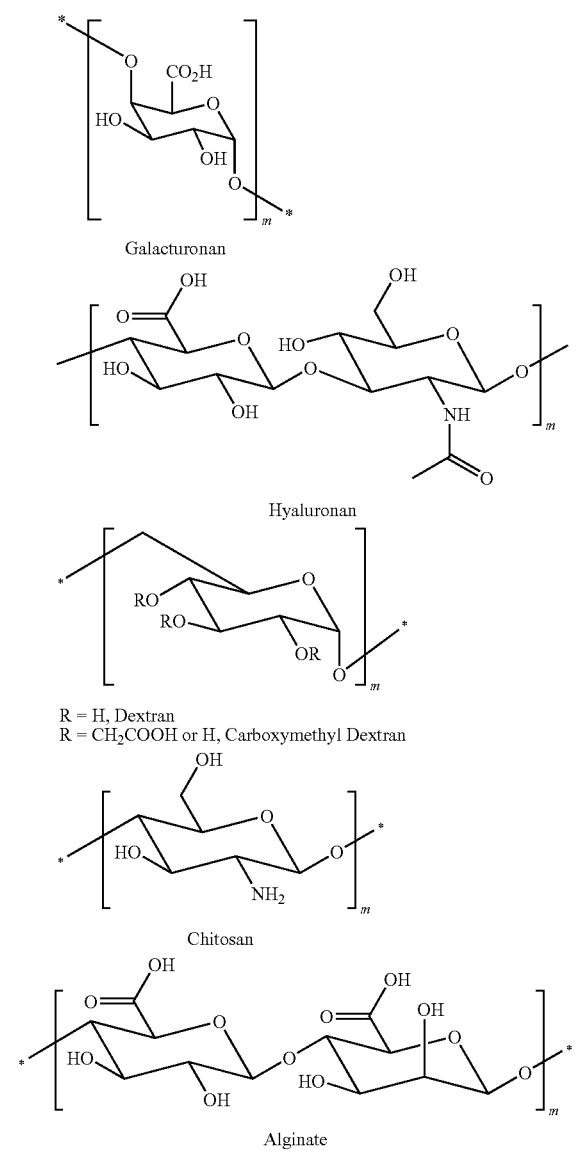

R = H, Dextran
R = CH$_2$COOH or H, Carboxymethyl Dextran

The polysaccharide may have an average degree of polymerisation m between 10 and 10,000.

In one embodiment, it has an average degree of polymerisation m between 10 and 1,000.

In another embodiment, it has an average degree of polymerisation m between 10 and 500.

In one embodiment, the invention also relates to an amphiphilic-BMP polymer complex characterised in that the hydrophobic group Hy is selected from the group consisting of the natural hydrophobic amino acids, selected from the group consisting of tryptophan, tyrosine, phenylalanine, leucine or isoleucine or the alcohol, ester, decarboxylated or amide derivatives thereof.

In one embodiment, the invention also relates to an amphiphilic-BMP polymer complex characterised in that the hydrophobic group Hy is tryptophan or an ester or amide derivative thereof.

Tryptophanol, tryptophanamide and 2-indolethylamine are examples of tryptophan derivatives.

In one embodiment, the amphiphilic-BMP polymer complex according to the invention is reversible.

The polymers used are synthesised according to the methods known by the person skilled in the art or are bought from suppliers, such as Sigma-Aldrich, NOF Corp. or CarboMer Inc.

The BMPs are selected from human recombinant BMPs obtained according to the methods known by the person skilled in the art or are bought from suppliers, such as Research Diagnostic Inc. (USA).

BMP is a highly hydrophobic growth factor. At physiological pH, the hydrophobicity of this protein leads to aggregation and then to precipitation. The amphiphilic-BMP polymer complexes according to the invention enable physical stabilisation of said protein in a solution at physiological pH.

Physical or chemical degradation means any physical event, such as aggregation, or chemical event, such as proteolysis, which leads to a decrease in the biological activity of the protein.

At the same time, physical or chemical stabilisation of the protein means the act of maintaining the biological activity of the protein.

The stability of the complex is monitored by measuring the stability of the BMP.

Stabilisation of the protein by means of an amphiphilic polymer may thus be proven, in particular by carrying out the following tests:
 a test for revealing the amphiphilic-BMP polymer complex by means of gel coelectrophoresis
 a test of thermal stability of the BMP in the presence of cells in the amphiphilic-BMP polymer complex carried out at 37° C. and at neutral pH
 a test of physical stability of the BMP in said complex at physiological pH.

The test for revealing the amphiphilic-BMP polymer complex by means of coelectrophoresis is based on displacing ions by using an electric field. The anionic complexes migrate towards the anode and the cationic complexes move towards the cathode. After migration, the proteins are transferred by capillarity to the PVDF membrane and are revealed by a specific antibody of the protein recognised by a second antibody coupled to the peroxidase. The protein which is alone does not migrate; the protein bound to the amphiphilic polymer migrates towards the anode or the cathode as a function of the total charge of the complex.

The test of thermal stability of the BMP in the presence of cells is carried out at 37° C. at neutral pH and involves depositing a BMP solution in a culture medium containing C2C12 myoblasts. The concentration of BMP in solution is determined by ELISA assay after the deposit (day 2) has been made and after 5 days (day 7) of culture. The biological activity of the BMP is evaluated by assaying the activity of the phosphatase alkaline produced between day 2 and day 7 during differentiation of the myoblasts into osteoblasts.

The test for physical stabilisation of a BMP at physiological pH is based on bringing a protein solution to physiological pH by exchanging the original buffer of the protein, generally at an acidic pH, with a PBS solution with a pH of 7.4. Three exchanges are carried out whilst keeping the BMP at a constant concentration at the end of the exchange. The concentration of the BMP in solution at the end of the process is determined by ELISA assay after centrifugation. This test may also be carried out by diluting a concentrated BMP-2 solution with a buffer fixing the pH at 7.4.

The amphiphilic-BMP polymer complex according to the invention is formed by placing a BMP and an amphiphilic polymer in an aqueous solution at physiological pH and in the absence of any organic solvent which may denature the protein. The formation of the amphiphilic-BMP polymer complex is spontaneous and does not involve covalent binding between the BMP and the amphiphilic polymer. This association is made by weak bonds which are substantially hydrophobic and ionic interactions. This formation of a complex requires no organic solvent.

Other tests may optionally be carried out in order to enhance proof of the formation of the amphiphilic-BMP polymer complex according to the invention.
- a test for maintaining the tertiary structure of the BMP determined by circular dichroism
- a test of the stability of a BMP in the amphiphilic-BMP polymer complex according to the invention at physiological pH under stress. The stress may be a particular stirring method, the presence of salts, etc.
- a test of resistance to proteolysis enzymes, such as thermolysin.

One of the problems solved by the invention is improved stability of the protein and therefore maintained biological activity in vitro and in vivo. Said biological activity may be evaluated by different tests showing the ability of a BMP to differentiate myoblasts into osteoblasts. Said differentiation may be measured by means of:
- the assay of the activity of the alkaline phosphatase produced in a cell culture.
- the staining of the cells producing the alkaline phosphatase.
- RT-PCR of the RNA of the osteocalcin produced in a cell culture.

The invention also relates to a therapeutic composition, characterised in that it comprises an amphiphilic-BMP polymer complex according to the invention.

Therapeutic composition means a composition which may be used in human or veterinary medicine.

The pharmaceutical composition according to the invention is preferably a composition to be applied locally and which may be present in the form of a solute, a gel, a cream, a lyophilisate, a powder or a paste.

The nature of the excipients which may be formulated with the amphiphilic-BMP polymer complex according to the invention is selected as a function of the dosage form thereof according to the general knowledge of the galenist.

Thus, when the composition according to the invention is in the form of a paste, said paste is obtained, for example, from products such as carboxymethyl celluloses (CMC), tricalcium phosphate and collagen.

Other excipients may be used in this invention in order to adjust the parameters of the formulation as a buffer for adjusting pH, an agent enabling adjustment of isotonicity, preservatives such as methyl parahydroxybenzoate, propyl parahydroxybenzoate, m-cresol, or phenol or even an antioxidant agent such as L-lysine hydrochloride.

According to the invention, the therapeutic composition is characterised in that it enables administration of approximately 1.5 mg/ml of BMP.

The present invention also relates to the use of an amphiphilic-BMP polymer complex according to the invention for the preparation of a therapeutic composition for inducing bone formation in vivo.

The invention also relates to a therapeutic treatment method for human or veterinary use, characterised in that it consists of administering, at the treatment site, a therapeutic composition comprising the amphiphilic-BMP polymer complex according to the invention.

Synthesis of Amphiphilic Polymers

EXAMPLE 1

Carboxymethyl Dextran Modified By Tryptophan Ethyl Ester (AP 1)

This amphiphilic polymer was synthesised from a carboxymethyl dextran with a degree of substitution with carboxymethyl per saccharide unit of 1.0 and an average molar mass of 60 kg/mol. The tryptophan ethyl ester was grafted onto the acids of this polymer according to a conventional coupling method in an organic solvent using ethyl chloroformate and N-Methylmorpholine. After diluting the reaction medium in water and adjusting the pH to 7 by adding NaOH 1N, the polymer was purified by ultrafiltration. The final polymer is characterised by:
- a degree of substitution with TrpOEt per saccharide unit of 0.45, determined by RMN $^1$H in $D_2O$/NaOD.
- a degree of substitution with carboxylates (methyl carboxylate) per saccharide unit of 0.55, determined by potentiometric assay.

EXAMPLE 2

Carboxymethyl Dextran Modified By Tryptophan, Sodium Salt (AP 2)

This amphiphilic polymer was obtained by basic hydrolysis of AP 1. Soda 1N (3.79 ml) was added to an aqueous solution of the amphiphilic polymer 1 (64 ml at 31 mg/ml) to obtain a pH of 12.7. The solution obtained was stirred for one night at ambient temperature. The polymer was purified by means of dialysis against water (NaCl 0.9% and $H_2O$). The final polymer is characterised by:
- a degree of substitution with TrpONa per saccharide unit of 0.45, determined by RMN $^1$H in $D_2O$/NaOD.
- a degree of substitution with carboxylates (methyl carboxylate, tryptophan carboxylate) per saccharide unit of 1.0, determined by potentiometric assay.

EXAMPLE 3

Carboxymethyl Dextran Modified By Phenylalanine Ethyl Ester (AP 3)

This amphiphilic polymer was synthesised according to example 1 from a carboxymethyl dextran with a degree of substitution with carboxymethyl per saccharide unit of 1.0 and an average molar mass of 60 kg/mol. The final polymer is characterised by:
- a degree of substitution with PheOEt per saccharide unit of 0.45, determined by RMN $^1$H in $D_2O$/NaOD.

a degree of substitution with carboxylates (methyl carboxylate) per saccharide unit of 0.55, determined by potentiometric assay.

EXAMPLE 4

Carboxymethyl Dextran Modified By Tyrosine Methyl Ester (AP 4)

This amphiphilic polymer was synthesised according to example 1 from a carboxymethyl dextran with a degree of substitution with carboxymethyl per saccharide unit of 1.0 and an average molar mass of 60 kg/mol. The final polymer is characterised by:
  a degree of substitution with TyrOMe per saccharide unit of 0.45, determined by RMN $^1$H in $D_2O$/NaOD.
  a degree of substitution with carboxylates (methyl carboxylate) per saccharide unit of 0.55, determined by potentiometric assay.

EXAMPLE 5

Dextran Succinic Acid Modified By Tryptophan Ethyl Ester (AP 5)

This amphiphilic polymer was synthesised from a dextran succinic acid with a degree of substitution with succinic acid per saccharide unit of 1.0 and an average molar mass of 70 kg/mol obtained according to the article by (Sanchez-Chaves, Manuel et al,. polymer 1998, 39 (13), 2751-2757.). The tryptophan ethyl ester was grafted onto the acids of this polymer according to a conventional coupling method in an organic solvent using ethyl chloroformate and N-Methylmorpholine. After diluting the reaction medium in water and adjusting the pH to 7 by adding NaOH 1N, the polymer was purified by ultrafiltration. The final polymer is characterised by:
  a degree of substitution with TrpOEt per saccharide unit of 0.45, determined by RMN $^1$H in $D_2O$/NaOD.
  a degree of substitution with carboxylates (succinic carboxylate) per saccharide unit of 0.55, determined by potentiometric assay.

COUNTER-EXAMPLE 1

Carboxymethyl Dextran Modified By Dodecylamine (AP 6)

This amphiphilic polymer was synthesised according to example 1 from a carboxymethyl dextran with a degree of substitution with carboxymethyl per saccharide unit of 1.0 and an average molar mass of 60 kg/mol. The final polymer is characterised by:
  a degree of substitution with dodecylamine per saccharide unit of 0.10, determined by RMN $^1$H in $D_2O$/NaOD.
  a degree of substitution with carboxylates (methyl carboxylate) per saccharide unit of 0.90, determined by potentiometric assay.

COUNTER-EXAMPLE 2

Carboxymethyl Dextran Modified By Benzylamine (AP 7)

This amphiphilic polymer is described in patent FR2794649A and is characterised by:
  a degree of substitution with benzylamine per saccharide unit of 0.45,
  a degree of substitution with carboxylates (methyl carboxylate) per saccharide unit of 0.55.

Affinity of BMP-2 for an Amphiphilic Polymer by Coelectrophoresis

Preparation of the BMP-2/Amphiphilic Polymer Complex

5 µl of a 0.28 mg/ml BMP-2 solution in a $H_2O$/AcN/TFA (64.9/35/0.1%) buffer were added to 7 µl of a buffered 100 mg/ml AP solution with a pH of 7.4. This solution was brought to 14 µl with a 0.9% NaCl solution. This solution had a concentration of BMP-2 of 0.1 mg/ml and a BMP-2/AP ratio of 1:500. This solution was lightly stirred for 30 minutes at ambient temperature.

Demonstration of the BMP-2/Amphiphilic Polymer Complex

The BMP-2/AP solution was diluted 20 times in a migration buffer (tris-acetate solution with a pH of 7). 2 µl of the diluted solution were then added to 8 µl of water and 7 µl of loading buffer (glycerol, tris-acetate and bromophenol blue in water). These 17 µl containing 10 ng of BMP-2 and 5 µl of AP were deposited in a well of a 0.8% agarose gel. The electrophoresis chamber was closed and the generator was set to 30V. Migration lasted for 1 hour.

After migration, the gel was transferred to a PVDF membrane placed on the anode under an electric field (20 minutes, 15V, Trans-Blot SD from BioRad). The membrane was saturated with skimmed milk for 1 hour at ambient temperature and then incubated with the primary antibodies of the BMP-2 (for one night at 4° C.) and finally was incubated with the secondary antibodies, rabbit anti goat HRP (for 1 hour at ambient temperature). Development was carried out by reacting the HRP on the Opti-4CN. Development was stopped when the staining was sufficient, since the reaction product absorbs in the visible.

When the BMP-2 forms a complex with the AP, the complex is detected in the form of a single spot 0.7 cm from the deposit (migration towards the anode). When the BMP-2 is alone or does not form a complex with the AP, it is detected at the place of the deposit and therefore has not migrated.

The results for the 5 polymers are shown in the following table.

| Amphiphilic Polymer | Migration |
| --- | --- |
| None | No |
| AP 1 | Yes |
| AP 2 | Yes |
| AP 3 | Yes |
| AP 4 | Yes |
| AP 5 | Yes |
| AP 6 | No |
| AP 7 | No |

Stability of BMP-2 in the Presence of an Amphiphilic Polymer at Physiological pH Preparation of the BMP-2/Amphiphilic Polymer Complex Starting with a 0.28 mg/ml BMP-2 solution in a $H_2O$/AcN/TFA (64.9/35/0.1%) buffer, different solutions were prepared:
1. a 0.084 mg/ml BMP-2 solution obtained by dilution in water
2. a 0.084/9.8 mg/ml BMP-2/amphiphilic polymer solution obtained by diluting the BMP-2 with a 14 mg/ml AP solution.

Each solution was then diluted at 1:10 with a PBS 10 mM solution with a pH of 7.4 and 300 mOsm and was then reconcentrated by means of Microcon cell centrifugation (YM10, 10 kD, 500 µl). This operation was repeated twice. After these three washes, each solution was centrifuged and the concentration of BMP-2 in the supernatant was determined by ELISA assay.

A portion of the 0.084 mg/ml BMP-2 solution did not undergo any washing, so as to serve as a control. Another portion of the 0.084 mg/ml BMP-2 solution underwent three cycles of washing with a HCl 1 mM solution (pH 3). This buffer is known for stabilising BMP-2 but is not compatible with a pharmaceutical application.

The ELISA assay of the BMP-2 solution which did not undergo any washing gave a concentration of BMP-2 of 83.4 µl. This value corresponds to 100% BMP-2. The concentrations determined by ELISA of the other solutions at the end of three washes with PBS were added to this value of the unwashed BMP-2. The percentages of BMP-2 yielded are shown in the following table.

| Solution | % of BMP-2 present |
| --- | --- |
| BMP-2 | 2 |
| BMP-2/AP 1 | 68 |
| BMP-2/AP 2 | 90 |
| BMP-2/AP 3 | 68 |
| BMP-2/AP 4 | 51 |
| BMP-2/AP 6 | 0 |

The APs which are able to form a complex with BMP-2 render the BMP-2 stable at physiological pH. In the absence of AP, BMP-2 is no longer present in a solution at physiological pH. Likewise, in the presence of an AP which does not form a complex with the BMP-2, the protein is no longer present in solution.

Stability and Biological Activity of BMP-2 in the Presence of an Amphiphilic Polymer in a Culture Medium at 37° C. and at Physiological pH On day 0, the C2C12 cells (muscle cells of mice) were seeded (7,000 cells per well) into 96-well culture plates containing DMEM containing 10% FVS and 1% TBA and were then placed in an oven for 24 hours. On day 1, after adhesion of the cells, the medium was replaced with DMEM containing 2% FVS and 1% TBA for 24 hours. On day 2, the medium was replaced with DMEM containing 2% FVS and 1% TBA supplemented with a solution of BMP-2 only (0.3 µm/ml) or a solution of the BMP-2/AP 1 complex (0.3/150 µm/ml, ratio 1:500). The complex was prepared by diluting the BMP-2 and the AP separately in the DMEM containing 2% FVS and 1% TBA. The protein/AP 1 mixture was left to rest for 1 hour before being deposited.

On day 7, i.e. 5 days after being deposited, the supernatant was sampled in order to assay the residual BMP-2 by ELISA.

| | % of BMP-2 in the supernatant | |
| --- | --- | --- |
| | Deposit | Deposit + 5 days |
| BMP-2 only | 100 | 2 |
| BMP-2/AP 1 | 100 | 41 |

Five days after contacting the cells, less than 5% of the BMP-2 which was alone remained, whereas more than 40% BMP-2 remained when it was mixed with AP 1.

On day 7 of the same experiment, the cells were washed twice with PBS then lysed with 50 µm of lysis buffer and underwent 3 cycles of freezing (−80° C.)/thawing (37° C.). The enzyme activity of the alkaline phosphatase was measured in the lysates on a substrate, p-nitrophenyl phosphate, which absorbs at 405 nm. This activity was reduced to the amount of proteins measured by microBCA and is therefore expressed in nmol pnP/min. µg of proteins.

| | ALP Activity (nmol pnP/µg protein.min) |
| --- | --- |
| BMP-2 only | 0.9 ± 0.12 |
| BMP-2/AP 1 | 1.7 ± 0.05 |

BMP-2 is stabilised by the complex in living conditions for more than five days, but it is not stable on its own for such a duration.

BMP-2 activity is revealed by a slow process of cellular differentiation, the BMP-2 complex being more active in vitro than BMP-2 alone.

Protection by Means of the BMP-2 Polymer Against Enzymatic Degradation

Preparation of the BMP-2/Polymer Complex

19 µl of a 0.315 mg/ml BMP-2 solution in a TFA acetonitrile buffer were added to 4.6 µl of a 66 mg/ml polymer (PA 2) solution, to 50 µl of Tris 50 mM with a pH of 7.5, to 60 µl of 25 µg/ml thermolysin and to 366.4 µl of $H_2O$. A similar solution not containing any polymer was prepared as a control. In these two solutions thermolysin represented 25% of the protein (weight/weight).

Digestion Kinetics:

The solutions of BMP-2 alone and of the complex containing thermolysin were incubated at 60° for 6 hours. 20 µl samples were taken at T=0, 20 min, 1 hr, 2 hrs and 6 hrs. When each sample was taken, 5 µl of 250 mM EDTA were immediately added, i.e. a final concentration of 50 mM, in order to inhibit the enzymatic reaction. The sample was then frozen at −20° C.

Development:

Development was carried out using a western-blot formed from 15% SDS-Page gel. 7 µl of each sample (containing 65 ng of BMP-2) were mixed with 7 µl of a Laemmli loading buffer containing SDS. The samples were then denatured for 10 min at 95° C. then deposited on the 15% SDS-Page gel. As a control, equivalent amounts of BMP-2 (65 ng) and of thermolysin (16.25 ng) were also deposited on the gel. The electrophoresis chamber was closed and the generator was set to 125 V. Migration lasted for 1 hr 15 min.

After migration, the gel was transferred to a PVDF membrane by means of a BioRad transfer system for 1 hr at 100 volts. The membrane was then saturated with skimmed milk for 1 hour at ambient temperature and then incubated with the primary antibodies of the BMP-2 (for one night at 4° C.) and finally was incubated with the secondary antibodies coupled with HRP (for 1 hour ambient temperature). Development was carried out by reacting the HRP on the Opti-4CN. Development was stopped when the staining was sufficient, since the reaction product absorbs in the visible.

When the BMP-2 is alone, the appearance of a band of a molecular weight which is lower after 20 minutes is observed, and this translates into degradation of the protein by thermolysin. In the presence of a polymer, this band is not present, which indicates that the polymer protects the protein against degradation After having checked that the polymer does not inhibit the action of the thermolysin, it may be concluded that the results obtained therefore show that the polymer PA 2 effectively protects BMP-2 against enzymatic degradation.

Solubilisation of BMP-2 in the Form of a Complex in Water at Physiological pH

Solubility of BMP-2 at Physiological pH

BMP-2 has an isoelectric point of 8.5, which means that, at a physiological pH, BMP-2 is close to its minimum solubility. This may be demonstrated by an experiment to neutralise an acid solution using BMP-2.

A clear 1.5 mg/mL BMP-2 solution was prepared in an acid buffer (Infuse buffer, pH 4.5). This solution was neutralized by adding a phosphate buffer in order to obtain a pH of 7.4 (final BMP-2 concentration of 1.2 mg/mL). At pH 7.4, BMP-2 has precipitated, and formed aggregates are visible. The neutralization has led to a suspension.

Solubility of the BMP-2/PA 2 Complex at Physiological pH

A clear 1.5 mg/mL BMP-2 solution was prepared in an acid buffer (Infuse buffer, pH 4.5). The lyophilised PA 2 was added to this solution in order to obtain a PA 2 concentration of 75 mg/mL. This BMP-2/PA 2 complex solution was then neutralised by adding a phosphate buffer in order to obtain a pH of 7.4 (final BMP-2 concentration of 1.2 mg/mL and final PA 2 concentration of 60 mg/mL). At pH 7.4, BMP-2 is completely soluble and no aggregate is visible. The solubility of BMP-2 at physiological pH in the form of a BMP-2/PA 2 complex is therefore greatly increased.

The invention claimed is:

1. An amphiphilic polymer-BMP complex comprised of an amphiphilic polymer and a BMP, wherein the BMP is in the form of a complex with the amphiphilic polymer as confirmable by gel coelectrophoresis and wherein the amphiphilic polymer-BMP complex is physically and chemically stable, and completely soluble in water at physiological pH at a BMP concentration of 1.2 mg/ml, and wherein:

the amphiphilic polymer is formed of a hydrophilic polysaccharide skeleton that includes hydrophobic substituents and hydrophilic groups according to the following general formula (I):

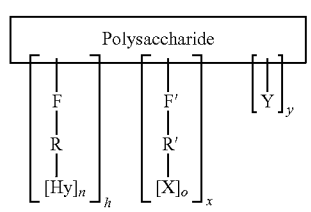

(I)

R and R', which may be the same or different, represent a bond or a chain comprising from 1 to 18 carbon atoms, said chain optionally being branched and/or unsaturated and optionally comprising one or more heteroatoms, F and F', which may be the same or different, represent an ester, a thioester, an amide, a carbonate, a carbamate, an ether, a thioether or an amine, X represents a hydrophilic group selected from the group consisting of carboxylates, sulphates, sulphonates, phosphates and phosphonates, Y represents a hydrophilic group selected from the group consisting of sulphates, sulphonates, phosphates and phosphonates, Hy represents a hydrophobic group selected from the group consisting of:

linear or branched $C_8$ to $C_{30}$ alkyls which may be unsaturated and/or contain one or more heteroatoms, linear or branched $C_8$ to $C_{18}$ alkylaryls or a linear or branched $C_8$ to $C_{18}$ arylalkyl which may be unsaturated and/or may contain one or more heteroatoms, $C_8$ to $C_{30}$ polycycles which may be unsaturated and/or may contain one or more heteroatoms, and excluding benzylamine, n and o are from 1 to 3, h represents the mole fraction of $[F-R-[Hy]_n]$ with respect to a monomer unit of the polysaccharide, from 0.01 to 0.5, x represents the mole fraction of $[F'-R'-[X]_o]$ with respect to a monomer unit of the polysaccharide, from 0 to 2.0, y represents the mole fraction of $[Y]$ with respect to a monomer unit of the polysaccharide, and is 0, the BMP is selected from the group of therapeutically active BMPs (bone morphogenetic proteins), and the amphiphilic polymer/BMP mass ratio is lower than or equal to 700.

2. Complex according to claim 1, wherein X is a carboxylate.

3. Complex according to claim 1, wherein the amphiphilic polymer/BMP mass ratio is lower than or equal to 500.

4. Complex according to claim 1, wherein the BMP is selected from the group consisting of BMP-2 (diberminalfa), BMP-4, BMP-7 (eptotermin alfa), BMP-14 and GDF-5.

5. Complex according to claim 1, wherein the amphiphilic polymer is selected from polymers in which the substituents are distributed in an arbitrary manner.

6. Complex according to claim 1, wherein the polysaccharide in general formula (I) is selected from the group consisting of hyaluronans, alginates, chitosans, galacturonans, chondroitin-sulphate, dextrans and celluloses.

7. Complex according to claim 1, wherein the polysaccharide in general formula (I) is a cellulose.

8. Complex according to claim 1, wherein the polysaccharide in general formula (I) is a dextran.

9. Complex according to claim 1, wherein the polysaccharide in general formula (I) is selected from the group consisting of hyaluronans, alginates and chitosans.

10. Complex according to claim 1, wherein the hydrophobic group Hy is a natural hydrophobic amino acid selected from the group consisting of tryptophan, tyrosine, phenylalanine, leucine, isoleucine and alcohol derivatives, decarboxylated derivatives, ester derivatives or amide derivatives thereof.

11. Complex according to claim 1, wherein the hydrophobic group Hy is tryptophan or an ester derivative or an amide derivative of tryptophan.

12. Complex according to claim 1, wherein the BMP in the amphiphilic polymer-BMP complex is stable at physiological pH.

13. Complex according to claim 1, wherein the BMP shows biological activity at 37° C. and neutral pH.

14. Complex according to claim 1, wherein x is from >0 to 2.0.

15. Complex according to claim 14, wherein X is a carboxylate.

16. Complex according to claim 1, wherein absent formation of the amphiphilic polymer-BMP complex, the BMP would aggregate and not form a solution in water at physiological pH.

17. Complex according to claim 1, wherein the amphiphilic polymer is (1) carboxymethyl dextran grafted with tryptophan ethyl ester, (2) carboxymethyl dextran grafted with tryptophan, sodium salt, (3) carboxymethyl dextran grafted with phenylalanine ethyl ester, (4) carboxymethyl dextran grafted with tyrosine ethyl ester or (5) dextran succinic acid grafted with tryptophan ethyl ester.

18. Process for preparing the amphiphilic polymer-BMP complex according to claim 1, wherein the amphiphilic polymer-BMP complex is formed and dissolved in an aqueous medium and in the absence of organic solvents which might denature the protein.

19. Process according to claim 18, wherein the formation of the amphiphilic polymer-BMP complex is reversible.

20. Therapeutic composition comprised of the amphiphilic polymer-BMP complex according to claim 1.

21. Therapeutic composition according to claim 20, wherein the therapeutic composition enables administration of approximately 1.5 mg per ml of BMP.

22. A method of inducing bone formation in vivo, the process comprised of administering to a human or an animal the therapeutic composition according to claim 20 in an amount effective to induce bone formation.

23. A method of inducing bone formation in vivo, the process comprised of administering to a human or an animal the amphiphilic polymer-BMP complex according to claim 1 in an amount effective to induce bone formation.

24. A solution comprising the amphiphilic polymer-BMP complex according to claim 1 and water, wherein the amphiphilic polymer-BMP complex is dissolved in the water at physiological pH.

25. The solution according to claim 24, wherein the solution is free of any organic solvents that might denature the BMP.

26. A method of inducing bone formation in vivo, the process comprised of administering to a human or an animal the solution according to claim 24 in an amount effective to induce bone formation.

* * * * *

UNITED STATES PATENT AND TRADEMARK OFFICE
CERTIFICATE OF CORRECTION

PATENT NO. : 8,389,661 B2  
APPLICATION NO. : 12/219679  
DATED : March 5, 2013  
INVENTOR(S) : Gerard Soula et al.

Page 1 of 1

It is certified that error appears in the above-identified patent and that said Letters Patent is hereby corrected as shown below:

In the Specification

Column 3, lines 6, 21, 26, 30, 40, 50, 56 and 61, change "BM" to --BMP--.

Column 3, line 39, change "at." to --Pat.--.

Column 3, line 62, change "E" to --EP--.

Column 3, delete the space between lines 6-7, 21-22, 26-27, 30-31, 38-39, 40-41, 50-51, 56-57, 61-62, and 63-64, there should not be a new paragraph.

Column 4, lines 2, 6, 27, 30, 32, 36, 50-54, 59, 61, and 64, change "BM" to --BMP--.

Column 4, line 2, change "LAGAs" to --PLAGAs--.

Column 4, line 8, change "LAGA" to --PLAGA--.

Column 4, delete the space between lines 1-2, 2-3, 6-7, 7-8, 27-28, 30-31, 32-33, 36-37, 50-51, 51-52, 52-53, 53-54, 54-55, 59-60, 61-62 and 64-65, there should not be a new paragraph.

Column 5, line 1, change "BM" to --BMP--.

Signed and Sealed this  
Twenty-fifth Day of June, 2013

Teresa Stanek Rea  
*Acting Director of the United States Patent and Trademark Office*